(12) United States Patent
Okita

(10) Patent No.: US 12,276,267 B2
(45) Date of Patent: Apr. 15, 2025

(54) RIGIDITY VARIABLE APPARATUS, AND MANUFACTURING METHOD FOR RIGIDITY VARIABLE APPARATUS

(71) Applicant: OLYMPUS CORPORATION, Tokyo (JP)

(72) Inventor: Tatsuhiko Okita, Akiruno (JP)

(73) Assignee: OLYMPUS CORPORATION, Tokyo (JP)

( * ) Notice: Subject to any disclaimer, the term of this patent is extended or adjusted under 35 U.S.C. 154(b) by 828 days.

(21) Appl. No.: 17/391,585

(22) Filed: Aug. 2, 2021

(65) Prior Publication Data

US 2021/0363977 A1 Nov. 25, 2021

Related U.S. Application Data

(63) Continuation of application No. PCT/JP2019/004184, filed on Feb. 6, 2019.

(51) Int. Cl.
*F03G 7/06* (2006.01)
*A61B 1/00* (2006.01)
*A61B 1/005* (2006.01)

(52) U.S. Cl.
CPC ............ *F03G 7/06143* (2021.08); *A61B 1/00* (2013.01); *A61B 1/0058* (2013.01); *F03G 7/06147* (2021.08)

(58) Field of Classification Search
None
See application file for complete search history.

(56) References Cited

U.S. PATENT DOCUMENTS

2007/0168018 A1* 7/2007 Amplatz .................. A61F 2/90
623/1.18
2017/0079508 A1 3/2017 Ikeda
(Continued)

FOREIGN PATENT DOCUMENTS

JP 59162262 A * 9/1984
JP H05-56910 A 3/1993
(Continued)

OTHER PUBLICATIONS

English translation of JP 59162262 (originally published Sep. 13, 1984), obtained from J-Plat Pat.*
(Continued)

*Primary Examiner* — George Wyszomierski
(74) *Attorney, Agent, or Firm* — Scully, Scott, Murphy & Presser, P.C.

(57) ABSTRACT

A rigidity variable apparatus includes: one or a plurality of coil units including a spiral-shaped coil portion in which a plurality of SMA element wires made of a shape-memory alloy are wound around an axis at a first pitch in a state where the SMA element wires are overlapped with each other in a predetermined axis direction, each of the SMA element wires memorizing a spiral shape with a pitch narrower than the first pitch, one of the plurality of SMA element wires starting to deform to the memorized spiral shape with a predetermined pitch when at a predetermined temperature or higher, another of the plurality of SMA element wires starting to deform to the spiral shape with a different pitch; and an electrothermal heater configured to heat the coil portion.

4 Claims, 3 Drawing Sheets

(56) References Cited

U.S. PATENT DOCUMENTS

2017/0182290 A1* 6/2017 Stern .................. A61M 25/005
2020/0016836 A1* 1/2020 Burnham ............... B33Y 40/00

FOREIGN PATENT DOCUMENTS

| JP | H05-207967 A | 8/1993 |
| JP | H06-67096 A | 3/1994 |
| JP | 2000-233027 A | 8/2000 |
| JP | 2000-262464 A | 9/2000 |
| JP | 2001-123937 A | 5/2001 |
| JP | 2004-121755 A | 4/2004 |
| JP | 2005-185526 A | 7/2005 |
| JP | 4161045 B2 * | 10/2008 |
| JP | 2014-167775 A | 9/2014 |
| JP | 2016-007434 A | 1/2016 |
| JP | 2019-001197 A | 1/2019 |
| WO | 2015/198761 A1 | 12/2015 |
| WO | 2017/094085 A1 | 6/2017 |
| WO | 2018/189855 A1 | 10/2018 |

OTHER PUBLICATIONS

English translation of JP 4161045-B2 (originally published Oct. 8, 208), obtained from PE2E search.*
English translation of JP 2014-167775 (originally published Sep. 11, 2014), obtained from PE2E search.*
International Search Report dated May 7, 2019 received in PCT/JP2019/004184.

* cited by examiner

RIGIDITY VARIABLE APPARATUS, AND MANUFACTURING METHOD FOR RIGIDITY VARIABLE APPARATUS

CROSS REFERENCE TO RELATED APPLICATION

This application is a continuation application of PCT/JP2019/004184 filed on Feb. 6, 2019, the entire contents of which are incorporated herein by this reference.

BACKGROUND OF THE INVENTION

1. Field of the Invention

The present invention relates to a rigidity variable apparatus using a shape-memory alloy, and a manufacturing method for the rigidity variable apparatus.

2. Description of the Related Art

In a medical field and an industrial field, for example, an insertion apparatus is used for observation or treatment of an inside of an insertion object such as a living body or a structural object. The insertion apparatus includes an insertion portion that has flexibility and that is inserted into an insertion object. The insertion apparatus includes an endoscope.

For example, WO 2017/094085 discloses a rigidity variable apparatus that changes difficulty of bending deformation (rigidity) of the insertion portion of the insertion apparatus. The rigidity variable apparatus disclosed in WO 2017/094085 can increase the rigidity of the insertion portion by heating a shape-memory alloy disposed in the insertion portion.

SUMMARY OF THE INVENTION

A rigidity variable apparatus according to an aspect of the present invention includes: one or a plurality of coil units including a spiral-shaped coil in which a first SMA element wire and a second SMA element wire are wound around an axis at a first pitch in a state where the first SMA element wire and the second SMA element wire are overlapped in a predetermined axis direction, the first SMA element wire and the second SMA element wire being made of a shape-memory alloy, the first SMA element wire memorizing a spiral shape with a second pitch narrower than the first pitch and being extended from the spiral shape with the second pitch to a spiral shape with the first pitch, the second SMA element wire memorizing a spiral shape with a third pitch narrower than the first pitch, and disposed along a gap between windings of the first SMA element wire extended to the spiral shape with the first pitch, the first SMA element wire and the second SMA element wire starting to deform to the memorized shapes when at a predetermined temperature or higher, the first SMA element wire starting to deform to the memorized spiral shape with the second pitch when at the predetermined temperature or higher, the second SMA element wire starting to deform to the memorized spiral shape with the third pitch when at the predetermined temperature or higher; and an electrothermal heater configured to heat the coil.

A manufacturing method for a rigidity variable apparatus according to an aspect of the present invention includes: causing a first SMA element wire to memorize a spiral shape with a second pitch, the first SMA element wire being made of a shape-memory alloy; causing a second SMA element wire to memorize a spiral shape with a third pitch, the second SMA element wire being made of a shape-memory alloy; extending the first SMA element wire to a spiral shape in which the first SMA element wire is wound at a first pitch wider than the second pitch, after causing the first SMA element wire to memorize the spiral shape with the second pitch; disposing the second SMA element wire along a gap between windings of the first SMA element wire extended to the spiral shape in which the first SMA element wire is wound at the first pitch, after causing the second SMA element wire to memorize the spiral shape with the third pitch, and forming a spiral-shaped coil in which the first SMA element wire and the second SMA element wire are wound around an axis at the first pitch in a state where the first SMA element wire and the second SMA element wire are overlapped in a predetermined axis direction; and disposing an electrothermal heater configured to heat the coil.

DETAILED DESCRIPTION OF THE PREFERRED EMBODIMENTS

Figure 1:
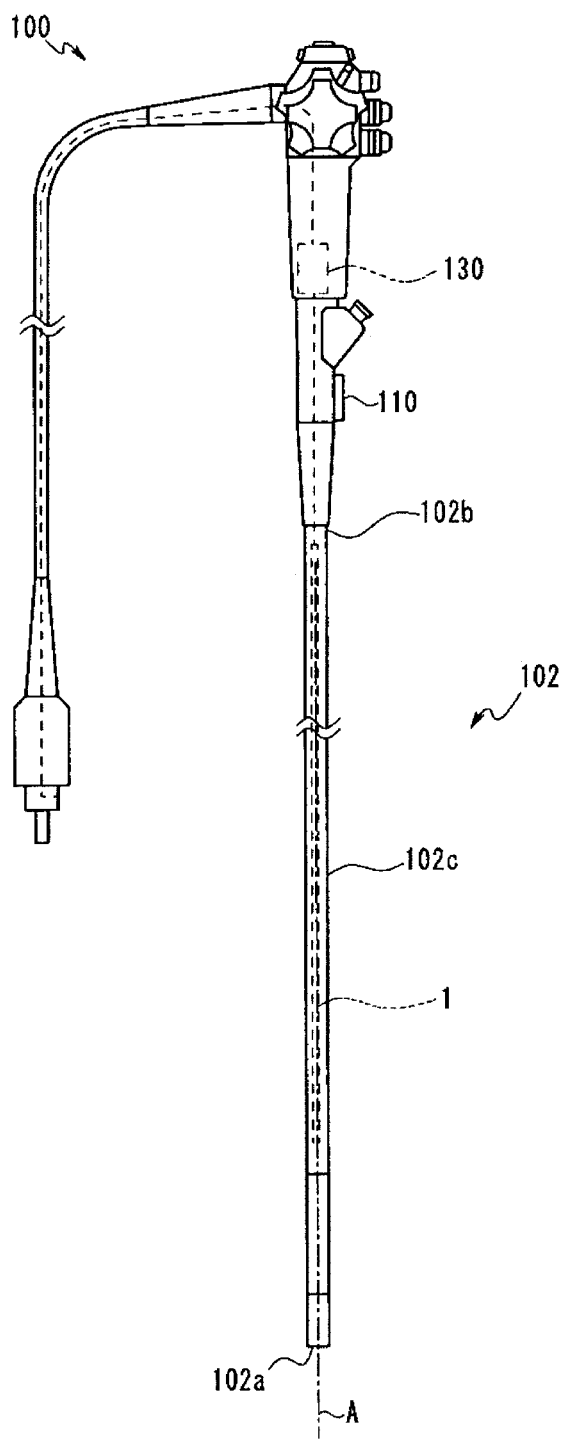
FIG. 1 is a diagram showing a configuration of an insertion apparatus in a first embodiment.

Preferred embodiments of the present invention will be described below with reference to the drawings. Note that in each drawing to be used below for description, scale differs for each component such that each component has a recognizable size in the drawing, and the present invention is not limited only to number of components, shapes of components, ratios of sizes of components and relative position relations of the respective components that are illustrated in the drawings.

First Embodiment

An example of the embodiment of the present invention will be described below. An insertion apparatus 100 shown in FIG. 1 includes an elongated insertion portion 102 that can be inserted into an insertion object such as a human body, and has a configuration for observing an inside of the insertion object, in the insertion portion 102. In other words, as an example of the embodiment, the insertion apparatus 100 is an endoscope. The insertion object into which the insertion portion 102 of the insertion apparatus 100 that is the endoscope is inserted is not limited to the human body, and may be another living body or may be an artifact such as a machine or a building. Further, the insertion apparatus 100 is not limited to the endoscope, and may be a treatment instrument or the like by which a medical treatment is performed in a living body.

The insertion portion 102 has an elongated shape. Hereinafter, an axis in a longitudinal direction of the elongated insertion portion 102 is referred to as a longitudinal axis A, The insertion portion 102 includes a flexible tube portion 102c having flexibility. The flexible tube portion 102c may include a so-called bending portion configured to actively bend and deform in response to user's operation of the insertion apparatus 100. Note that although the longitudinal axis A is shown as a straight line in FIG. 1, the longitudinal axis A deforms in response to the bending deformation of the insertion portion 102.

Hereinafter, an end on a side of the insertion portion 102 that is inserted into the insertion object is referred to as a distal end 102a, and an end opposite to the distal end 102a is referred to as a proximal end 102b. In other words, the insertion portion 102 is inserted into the insertion object from the distal end 102a. Further, a direction along the longitudinal axis A is referred to as an axis direction.

The insertion apparatus 100 includes a rigidity variable apparatus 1, an operation portion 110 and a control portion 130. The rigidity variable apparatus 1 is disposed at least at a part of the flexible tube portion 102c of the insertion portion 102. The operation portion 110 and the control portion 130 are components for controlling action of the rigidity variable apparatus 1.

The operation portion 110 is a push-button switch, for example, and is a component to which the user of the insertion apparatus 100 inputs an instruction for controlling the action of the rigidity variable apparatus 1. The operation portion 110 is electrically connected to the control portion 130.

The control portion 130 controls the action of the rigidity variable apparatus 1 described later, in response to the input of the instruction from the user to the operation portion 110. Note that electric power for operating the rigidity variable apparatus 1 and the control portion 130 is supplied from an external apparatus to which the insertion apparatus 100 is connected. The external apparatus is a video processor or a light source apparatus, for example. Note that the insertion apparatus 100 may include a battery configured to supply the electric power for operating the rigidity variable apparatus 1 and the control portion 130.

Note that although the operation portion 110 and the control portion 130 are provided in the insertion apparatus 100 as an example in the embodiment, one or both of the operation portion 110 and the control portion 130 may be provided in the external apparatus to which the insertion apparatus 100 is connected.

Figure 2:
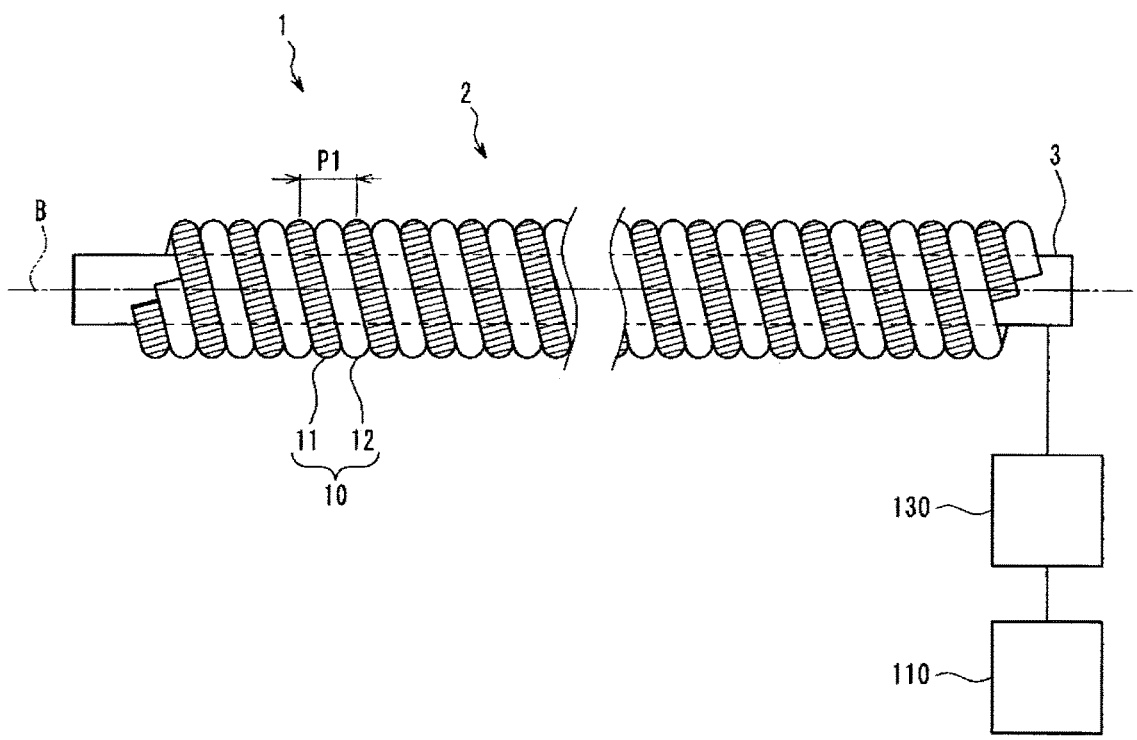
FIG. 2 is a diagram showing a configuration of a rigidity variable apparatus in the first embodiment.

FIG. 2 is a diagram showing a configuration of the rigidity variable apparatus 1. The rigidity variable apparatus 1 includes one or a plurality of coil units 2 and a heating portion 3.

The coil unit 2 has a shape that is elongated in a direction parallel to an axis B along the longitudinal axis A of the insertion portion 102. The rigidity variable apparatus 1 can change rigidity against an input of a force in a direction of bending of the axis B of the coil unit 2. The rigidity means difficulty in bending deformation of the elongated coil unit 2. The rigidity is expressed as a force necessary for bending a section with a predetermined length in a direction along the axis B of the coil unit 2 at a predetermined curvature. Accordingly, as the rigidity is higher, the deformation in the bending direction of the coil unit 2 is harder to occur.

The coil unit 2 includes one or a plurality of coil portions 10. Each coil portion 10 has a spiral shape in which a plurality of SMA element wires each made of a shape-memory alloy are wound around the axis B at a first pitch P1 in a state where the SMA element wires are overlapped in a predetermined axis B direction.

In the shape-memory alloy, for which detailed descriptions are omitted because of a known technique, phase change occurs at a predetermined temperature T, and elastic coefficient changes. The predetermined temperature T is higher than room temperature. Further, the shape-memory alloy exhibits superelasticity when at the predetermined temperature or higher.

Each of the SMA element wires included in the coil portion 10 memorizes a spiral shape with a pitch narrower than the first pitch P1, and starts to deform to the memorized shape when at the predetermined temperature T or higher. Note that pitches of the spiral shapes memorized by the respective SMA element wires may be identical or may be different.

More specifically, the coil portion 10 in the embodiment includes a first SMA element wire 11 that is a wire member made of a shape-memory alloy and a second SMA element wire 12 that is a wire member made of a shape-memory alloy. Note that the first SMA element wire 11 is hatched in FIG. 2 for easily discriminating between the first SMA element wire 11 and the second SMA element wire 12. In other words, the hatching in FIG. 2 does not show a cross-section surface.

Note that the first SMA element wire 11 and the second SMA element wire 12 may be composed of different shape-memory alloys. Further, cross-section shapes of the first SMA element wire 11 and the second SMA element wire 12 may be different. Further, one or both of surfaces of the first SMA element wire 11 and the second SMA element wire 12 may be covered by a coat having electric insulation.

The first SMA element wire 11 and the second SMA element wire 12 are spirally wound around the axis B at the first pitch P1 in a state where the first SMA element wire 11 and the second SMA element wire 12 are overlapped in the predetermined direction along the axis B. Herein, the pitch means an interval of the winding pitch of spiral first SMA element wire 11 (or the second SMA element wire 12) in a direction parallel to the axis B.

For more detail, the first SMA element wire 11 and the second SMA element wire 12 closely contact with each other in the direction parallel to the axis B. Further, the first pitch P1 is a value when the first SMA element wire 11 and the second SMA element wire 12 closely contacting with each other in the direction parallel to the axis B are closely wound. In other words, the first pitch P1 is the same as a value resulting from summing respective wire diameters of the first SMA element wire 11 and the second SMA element wire 12 in the direction parallel to the axis B.

The first SMA element wire 11 memorizes a spiral shape with a second pitch P2 narrower than the first pitch P1. In other words, the first SMA element wire 11 starts to deform such that the pitch becomes narrower when at the predetermined temperature T or higher. Similarly, the second SMA element wire 12 memorizes a spiral shape with a third pitch P3 narrower than the first pitch P1. In other words, the second SMA element wire 12 starts to deform such that the pitch becomes narrower when at the predetermined temperature T or higher. The second pitch P2 of the spiral shape memorized by the first SMA element wire 11 and the third pitch P3 of the spiral shape memorized by the second SMA element wire 12 may be the same, or may be different.

In the embodiment, as an example, the spiral shape memorized by the first SMA element wire 11 is a shape in which only the first SMA element wire 11 is closely wound. The spiral shape memorized by the second SMA element wire 12 is a shape in which only the second SMA element wire 12 is closely wound. In other words, in the coil portion 10, the first SMA element wire 11 and the second SMA element wire 12 that have closely-wound spiral shapes are combined in a state where the first SMA element wire 11 and the second SMA element wire 12 are extended until each of the pitches becomes the first pitch P1.

Note that the coil portion 10 may be configured by closely winding three or more SMA element wires made of a shape-memory alloy in a state where the three or more SMA element wires closely contact with each other in the direction parallel to the axis B.

The heating portion 3 heats the coil portion 10. A configuration of the heating portion 3 is not particularly limited, but in the embodiment, the heating portion 3 is an electrothermal heater, as an example. In the embodiment, as an example, the heating portion 3 has a shape that is elongated in the direction along the axis B, and is inserted into the coil portion 10. The heating portion 3 deforms with the deformation of the coil unit 2 in the bending direction. Note that one heating portion 3 or a plurality of heating portions 3 may be included in the rigidity variable apparatus 1. The heating portion 3 may be disposed in a periphery of the coil portion 10.

The heating portion 3 is operated to be capable of heating the coil portion 10 to the predetermined temperature T or higher. The heating portion 3 is electrically connected to the control portion 130, and action of the heating portion 3 is controlled by the control portion 130. The control portion 130 causes the heating portion 3 to operate in response to user's operation of the operation portion 110.

In the rigidity variable apparatus 1 having the above-described configuration, in a first state where the heating portion 3 is not operated and where the temperature of the coil portion 10 is lower than the predetermined temperature T, the elastic coefficients of the first SMA element wire 11 and second SMA element wire 12 configuring the coil portion 10 are low. Accordingly, in the first state, the rigidity of the coil unit 2 of the rigidity variable apparatus 1 is relatively low.

Further, in the rigidity variable apparatus 1 in the embodiment, in a second state where the heating portion 3 is operated and where the temperature of the coil portion 10 is the predetermined temperature T or higher, the elastic coefficients of the first SMA element wire 11 and second SMA element wire 12 configuring the coil portion 10 are high.

Further, in the second state, the first SMA element wire 11 and the second SMA element wire 12 start to deform to the spiral shapes with the second pitch P2 and third pitch P3 narrower than the first pitch P1. The first SMA element wire 11 and the second SMA element wire 12 closely contact with each other in the direction parallel to the axis B in the closely-wound state. Accordingly, in the second state, the first SMA element wire 11 and the second SMA element wire 12 start to deform to the spiral shapes with the second pitch P2 and the third pitch P3, and thereby, a compressive force to compress the coil portion 10 in the direction parallel to the axis B is generated while a total length of the coil portion 10 in the direction parallel to the axis B is not changed.

In the second state, the rigidity of the coil unit 2 is higher than in the first state, because of the generation of the compressive force and the increase in the elastic coefficients of the first SMA element wire 11 and the second SMA element wire 12 described above.

In this way, the rigidity variable apparatus 1 in the embodiment can change the rigidity of the coil unit 2, by switching whether the heating portion 3 is operated. Particularly, compared with a case where one wire member made of the shape-memory alloy is heated, the rigidity variable apparatus 1 in the embodiment can further increase the rigidity of the coil unit 2 in the second state.

Further, the coil portion 10 in the embodiment has a small heat capacity because the coil portion 10 is configured by the first SMA element wire 11 and the second SMA element wire 12 that have shapes of wires. Accordingly, a time period necessary for cooling the coil portion 10 to lower than the predetermined temperature from the state of the predetermined temperature T or higher is short. Consequently, the rigidity variable apparatus 1 can perform switching from a state where the rigidity of the coil unit 2 has been increased to a state where the rigidity has been decreased, in a short time period.

Furthermore, the insertion apparatus 100 includes the rigidity variable apparatus 1 described above, in the flexible tube portion 102c of the insertion portion 102, and therefore, can change the rigidity of the flexible tube portion 102c of the insertion portion 102, in response to user's operation of the operation portion 110.

Since the rigidity variable apparatus 1 in the embodiment can achieve both a high rigidity at the time when the rigidity of the coil unit 2 is increased and lowering of the rigidity in a short time period as described above, the insertion apparatus 100 can expand a change range of the rigidity of the flexible tube portion 102c of the insertion portion 102 and concurrently can shorten the time period necessary for the change in the rigidity.

Second Embodiment

A second embodiment of the present invention will be described below, Only differences from the first embodiment will be described below, the same components as those in the first embodiment are denoted by identical reference characters, and description for the same components will be omitted when appropriate.

Figure 3:
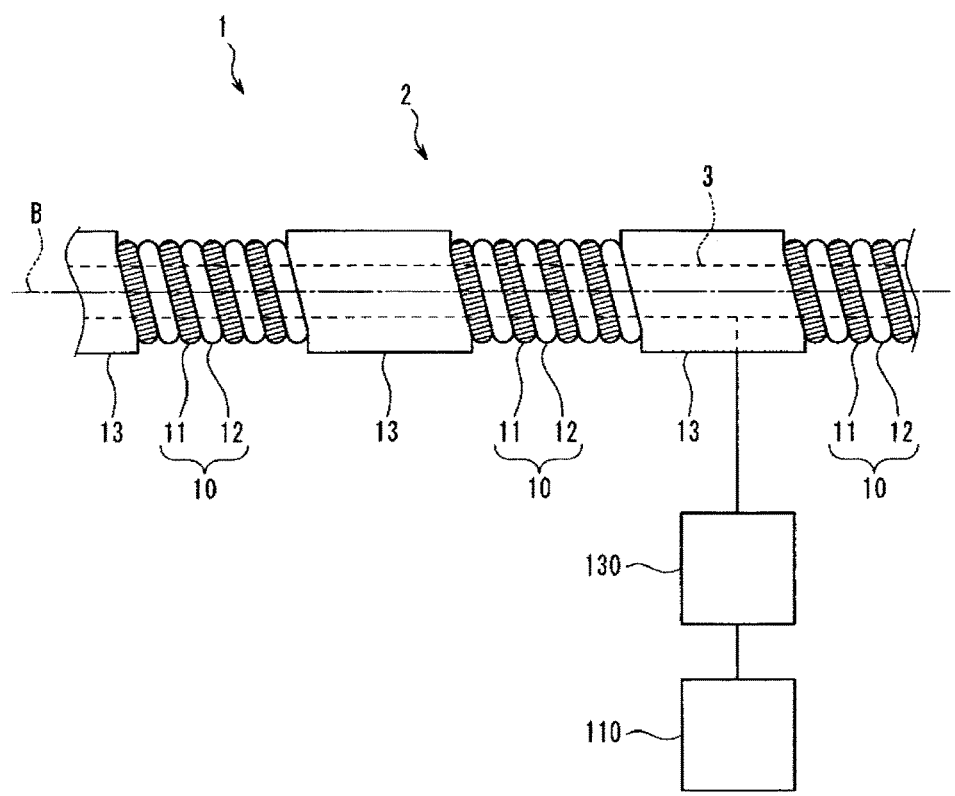
FIG. 3 is a diagram showing a configuration of a rigidity variable apparatus in a second embodiment.

An insertion apparatus 100 in the embodiment is different from the insertion apparatus 100 in the first embodiment, in the configuration of the rigidity variable apparatus 1. FIG. 3 is a diagram showing a configuration of a rigidity variable apparatus 1 in the embodiment.

A coil unit 2 of the rigidity variable apparatus 1 in the embodiment includes a plurality of coil portions 10, one or a plurality of high-rigidity portions 13, and a heating portion 3.

Similarly to the first embodiment, the plurality of coil portions 10 are configured by winding a plurality of SMA element wires each made of a shape-memory alloy around the axis B at the first pitch P1 in the state where the SMA element wires are overlapped in the predetermined axis B direction. In other words, each coil portion 10 has a configuration in which the first SMA element wire 11 and the second SMA element wire 12 are closely wound around the axis B in the state where the first SMA element wire 11 and the second SMA element wire 12 closely contact with each other in the direction parallel to the axis B. Note that each coil portion 10 may have a configuration in which three or more SMA element wires are closely wound around the axis B in a state where the SMA element wires closely contact with each other in the direction parallel to the axis B.

Each of the high-rigidity portions 13 is a member that joins the plurality of coil portions 10 in the direction along the axis B. Each of the high-rigidity portion 13 has a higher rigidity than the coil portion 10 when at the predetermined temperature T or higher. The heating portion 3 can heat the plurality of coil portions 10 to the predetermined temperature 1 or higher.

Since the plurality of coil portions 10 are joined by the high-rigidity portions 13 having a higher rigidity than the coil portion 10, the rigidity variable apparatus 1 in the embodiment can increase the rigidity of the coil unit 2 in a second state where the plurality of coil portions 10 are heated to the predetermined temperature T or higher, compared with the first embodiment.

Third Embodiment

A third embodiment of the present invention will be described below. Only differences from the first embodiment will be described below, the same components as those in the first embodiment are denoted by identical reference characters, and description for the same components will be omitted when appropriate.

Figure 4:
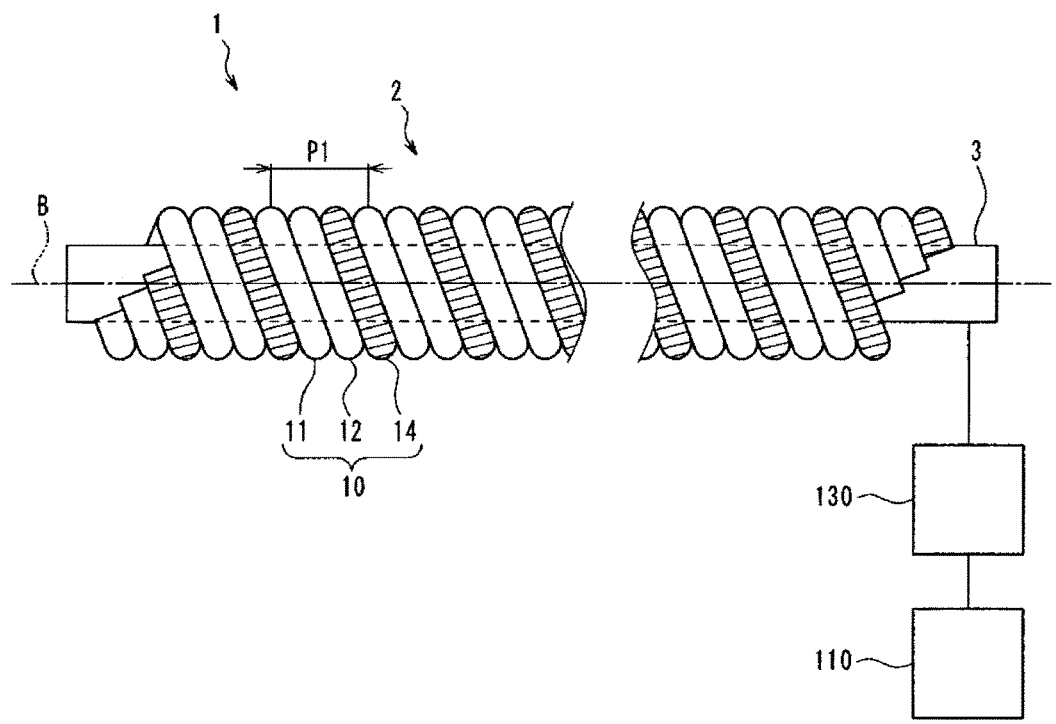
FIG. 4 is a diagram showing a configuration of a rigidity variable apparatus in a third embodiment.

An insertion apparatus 100 in the embodiment is different from the insertion apparatus 100 in the first embodiment, in the configuration of the rigidity variable apparatus 1. FIG. 4 is a diagram showing a configuration of a rigidity variable apparatus 1 in the embodiment.

A coil unit 2 of the rigidity variable apparatus 1 in the embodiment includes a coil portion 10 in which one or a plurality of metal element wires 14 made of metal are wound around the axis B together with the plurality of SMA element wires. A material composing the metal element wire 14 is not particularly limited, but it is preferable that the material composing the metal element wire 14 is a metal having a high heat conductivity. In the embodiment, as an example, the metal element wire 14 is composed of a copper alloy or an aluminum alloy.

Note that the metal element wire 14 is hatched in FIG. 4 for easily discriminating among the first SMA element wire 11, the second SMA element wire 12 and the metal element wire 14. In other words, the hatching in FIG. 4 does not show a cross-section surface.

More specifically, the coil portion 10 in the embodiment is configured by closely winding the first SMA element wire 11, the second SMA element wire 12 and the metal element wire 14 around the axis B in a state where the first SMA element wire 11, the second SMA element wire 12 and the metal element wire 14 are overlapped in the direction parallel to the axis B. In the embodiment, the first pitch P1 is the same as a value resulting from summing respective wire diameters of the first SMA element wire 11, the second SMA element wire 12 and the metal element wire 14 in the direction parallel to the axis B.

Similarly to the first embodiment, the rigidity variable apparatus 1 in the embodiment can change the rigidity of the coil unit 2, by switching whether to operate the heating portion 3. In the embodiment, since the metal element wire 14 contacts the SMA element wires 11, 12, it is possible to increase a heat release amount from the SMA element wires 11, 12 having a temperature of the predetermined temperature T or higher. Consequently, in the embodiment, it is possible to shorten the time period necessary for cooling the coil portion 10 to a temperature lower than the predetermined temperature T from the state of the predetermined temperature T or higher, compared with the first embodiment. In other words, the rigidity variable apparatus 1 in the embodiment can perform the switching from the state where the rigidity of the coil unit 2 has been increased to the state where the rigidity has been decreased, in a shorter time period, than the rigidity variable apparatus 1 in the first embodiment.

Note that the rigidity variable apparatus 1 in the embodiment may include a plurality of coil portions 10 and one or a plurality of high-rigidity portions 13 that join the plurality of coil portions 10, similarly to the second embodiment.

Fourth Embodiment

A fourth embodiment of the present invention will be described below. Only differences from the first embodiment will be described below, the same components as those in the first embodiment are denoted by identical reference characters, and description for the same components will be omitted when appropriate.

Figure 5:
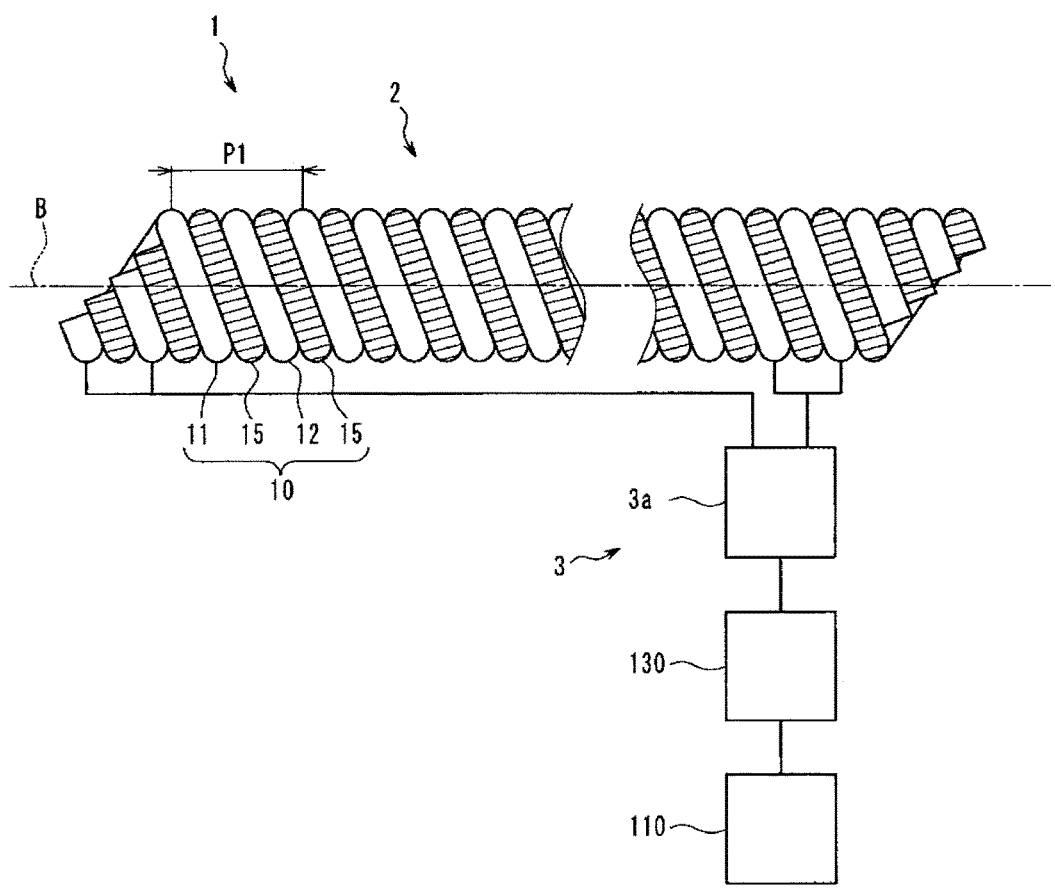
FIG. 5 is a diagram showing a configuration of a rigidity variable apparatus in a fourth embodiment.

An insertion apparatus 100 in the embodiment is different from the insertion apparatus 100 in the first embodiment, in the configuration of the rigidity variable apparatus 1. FIG. 5 is a diagram showing a configuration of a rigidity variable apparatus 1 in the embodiment.

A coil unit 2 of the rigidity variable apparatus 1 in the embodiment includes a coil portion 10 in which one or a plurality of insulating element wires 15 composed of electric insulating material are wound around the axis B together with the plurality of SMA element wires. A material composing the insulating element wire 15 is not particularly limited, but in the embodiment, as an example, the insulating element wire 15 is composed of a synthetic resin or ceramic.

Note that the insulating element wire 15 is hatched in FIG. 5 for easily discriminating among the first SMA element wire 11, the second SMA element wire 12 and the insulating element wire 15. In other words, the hatching in FIG. 5 does not show a cross-section surface.

More specifically, a coil portion 10 in the embodiment is configured by closely winding the first SMA element wire 11, the second SMA element wire 12 and the insulating element wire 15 around the axis B in a state where the first SMA element wire 11, the second SMA element wire 12 and the insulating element wire 15 are overlapped in the direction parallel to the axis B. In the embodiment, as an example, the coil portion 10 includes two insulating element wires 15. The two insulating element wires 15 are disposed so as to sandwich the first SMA element wire 11 in the direction parallel to the axis B. Accordingly, in the coil portion 10 in the embodiment, the first SMA element wire 11 and the second SMA element wire 12 are electrically insulated. In the embodiment, the first pitch P1 is the same as a value resulting from summing respective wire diameters of the first SMA element wire 11, the second SMA element wire 12 and the two insulating element wires 15 in the direction parallel to the axis B.

The heating portion 3 in the embodiment heats the coil portion 10 by performing energization of one or both of the first SMA element wire 11 and the second SMA element wire 12. In the embodiment, since the insulating element wire 15 is interposed between the first SMA element wire 11 and the second SMA element wire 12 that are closely wound, it is possible to cause the first SMA element wire 11 and the second SMA element wire 12 to generate heat, by performing the energization of one or both of the first SMA element wire 11 and the second SMA element wire 12 that are wire members.

The heating portion 3 includes an energization control apparatus 3b. At the time of operating, the energization control apparatus 3b performs the energization of one or both of the first SMA element wire 11 and the second SMA element wire 12. Electric power to be supplied to one or both of the first SMA element wire 11 and the second SMA element wire 12 is supplied from an external apparatus to which the insertion apparatus 100 is connected. Note that the insertion apparatus 100 may include a battery configured to supply electric power to one or both of the first SMA element wire 11 and the second SMA element wire 12.

In the rigidity variable apparatus 1 in the embodiment, one or both of the first SMA element wire 11 and the second SMA element wire 12 operate as a heater. Therefore, unlike the first embodiment, the rigidity variable apparatus 1 in the embodiment does not need to include a heater separately from the coil portion 10, allowing reduction in size. Further, in the embodiment, by reducing the size of the rigidity variable apparatus 1, it is possible to reduce the size of the insertion portion 102 of the insertion apparatus 100.

Note that the rigidity variable apparatus 1 in the embodiment may include a plurality of coil portions 10 and one or a plurality of high-rigidity portions 13 that join the plurality of coil portions 10, similarly to the second embodiment. Further, in the rigidity variable apparatus 1 in the embodiment, the coil portion 10 may include a metal element wire 14, similarly to the third embodiment.

The present invention is not limited to the above embodiments. When appropriate, modifications can be made without departing from the gist or idea of the invention that is read from the claims and the whole of the specification. The modified rigidity variable apparatuses and insertion apparatuses are also included in the technical scope of the present invention.

What is claimed is:

1. A rigidity variable apparatus comprising:
   one or more coil units including a spiral-shaped coil in which a first shape memory alloy (SMA) wire and a second SMA wire are wound alternately around an axis at a first pitch in a state where the first SMA wire and the second SMA wire contact each other in a predetermined axis direction, the first SMA wire and the second SMA wire being made of a shape-memory alloy, the first SMA wire memorizing a spiral shape with a second pitch narrower than the first pitch and being extended from the spiral shape with the second pitch to a spiral shape with the first pitch, the second SMA wire memorizing a spiral shape with a third pitch narrower than the first pitch, and disposed along a gap between windings of the first SMA wire extended to the spiral shape with the first pitch, the first SMA wire and the second SMA wire are configured to deform to the memorized shapes when at a predetermined temperature or higher, the first SMA wire is configured to deform to the memorized spiral shape with the second pitch when at the predetermined temperature or higher, the second SMA wire is configured to deform to the memorized spiral shape with the third pitch when at the predetermined temperature or higher; and
   an electrothermal heater configured to heat the coil.

2. The rigidity variable apparatus according to claim 1, wherein
   the one or more coil units comprise a plurality of coil units, and
   the rigidity variable apparatus further comprises one or more joining members that join the plurality of coil units in the axis direction, the one or more joining members having a higher rigidity than the plurality of coil units.

3. The rigidity variable apparatus according to claim 1, wherein the one or more coil units each include a spiral-shaped coil in which the first SMA wire, the second SMA wire, and one or more metal wires made of metal are wound around the axis at a fourth pitch in a state where the first SMA wire, the second SMA wire, and the one or more metal wires contact each other in that order in the axis direction, the fourth pitch being a value resulting from summing respective outer dimensions of the first SMA wire, the second SMA wire and the one or more metal wires in a direction parallel to the axis.

4. A rigidity variable apparatus comprising:
   one or more coil units including a spiral-shaped coil in which a first shape memory alloy (SMA) wire and a second SMA wire are wound alternately around an axis at a first pitch in a predetermined axis direction, the first SMA wire and the second SMA wire being made of a shape-memory alloy, the first SMA wire memorizing a spiral shape with a second pitch narrower than the first pitch and being extended from the spiral shape with the second pitch to a spiral shape with the first pitch, the second SMA wire memorizing a spiral shape with a third pitch narrower than the first pitch, and disposed along a gap between windings of the first SMA wire extended to the spiral shape with the first pitch, the first SMA wire and the second SMA wire are configured to deform to the memorized shapes when at a predetermined temperature or higher, the first SMA wire is configured to deform to the memorized spiral shape with the second pitch when at the predetermined temperature or higher, the second SMA wire is configured to deform to the memorized spiral shape with the third pitch when at the predetermined temperature or higher; and
   an electrothermal heater configured to heat the coil;
   wherein each of the one or more coil units includes a spiral-shaped coil in which the first SMA wire, the second SMA wire, and one or more insulating wires comprising an electric insulating material are wound around the axis at a fifth pitch in a state where the one or more insulating wires contact so as to be sandwiched between the first SMA wire and the second SMA wire in the axis direction, the fifth pitch being a value resulting from summing respective outer dimensions of the first SMA wire, the second SMA wire, and the one or more insulating wires in a direction parallel to the axis.

* * * * *